(12) United States Patent
Takase et al.

(10) Patent No.: US 7,270,783 B2
(45) Date of Patent: Sep. 18, 2007

(54) ANALYSIS SYSTEM AND ANALYSIS METHOD

(75) Inventors: Toshikazu Takase, Tokyo (JP); Keiji Eguchi, Tokyo (JP); Toshiaki Kato, Tokyo (JP)

(73) Assignee: JEOL Ltd., Tokyo (JP)

( * ) Notice: Subject to any disclaimer, the term of this patent is extended or adjusted under 35 U.S.C. 154(b) by 765 days.

(21) Appl. No.: 10/004,259

(22) Filed: Nov. 1, 2001

(65) Prior Publication Data

US 2002/0122745 A1    Sep. 5, 2002

(30) Foreign Application Priority Data

Nov. 1, 2000  (JP)  ............... 2000-334236
Oct. 3, 2001  (JP)  ............... 2001-307007

(51) Int. Cl.
*B32B 5/02*  (2006.01)
(52) U.S. Cl. .................. 422/63; 422/99; 422/100; 422/101; 422/64; 422/65; 436/43; 436/180
(58) Field of Classification Search .................. 436/43, 436/47, 48, 180; 422/63–67, 99–101
See application file for complete search history.

(56) References Cited

U.S. PATENT DOCUMENTS

| 4,835,707 | A | * | 5/1989 | Amano et al. | ............... 700/266 |
| 5,762,877 | A | * | 6/1998 | Brewer | ..................... 422/100 |
| 6,019,945 | A | * | 2/2000 | Ohishi et al. | .................. 422/65 |
| 6,716,320 | B1 | * | 4/2004 | Cole | .......................... 202/175 |

OTHER PUBLICATIONS

"Combinatorial Chemistry Redefining The Scientific Method", Stu Borman, *C&EN*, May 15, 2000, pp. 53-65.

* cited by examiner

*Primary Examiner*—Jill Warden
*Assistant Examiner*—Jyoti Nagpaul
(74) *Attorney, Agent, or Firm*—The Webb Law Firm (57) ABSTRACT

An analysis system which permits sample pretreatment which comprises: a sample rack; a sample container supply, a sample dispenser, a solvent-removing evaporator, a solvent dispenser for dispensing a second solvent, a sample-stirring means, a sample aspirating-and-transferring means, a sample recovery means, a sample container recovery means, and a control means for controlling the aforementioned various means.

19 Claims, 6 Drawing Sheets

ANALYSIS SYSTEM AND ANALYSIS METHOD

BACKGROUND OF THE INVENTION

1. Field of the Invention

The present invention relates to a system and a method in which sample treatment steps, including a solvent replacement step, are automated and performed in various analytical instruments, such as nuclear magnetic resonance (NMR) spectrometers, mass spectrometers, and spectroscopic instruments.

2. Description of the Related Art

In an NMR spectrometer, for example, it is always necessary to dissolve a sample under investigation in a deuterated solvent (e.g., deuterated chloroform, deuterated acetone, or deuterated water) or in a conventional protonated solvent containing more than a given amount (10%) of a deuterated solvent. One reason for this is that the deuteration is necessary for the NMR lock that stabilizes the instrument. Another reason is to prevent appearance of excessively strong NMR signals due to protonated (non-deutereated) solvent, such as chloroform, acetone, or $H_2O$; otherwise, the strong signals would overlap a signal of interest or the detection sensitivity would deteriorate. However, in high performance liquid chromatography (HPLC) or other similar technique, a protonated solvent is generally used as a mobile phase and so it is not easy to replace the protonated solvent by a deuterated solvent. Consequently, it is necessary that the protonated solvent is evaporated off, the sample is dried and solidified, and then is redissolved in a deuterated solvent. In the past, all of these sample pretreatment steps have been done by a human. That is, cumbersome manual operations have been performed.

In order to investigate samples by an NMR spectrometer by the prior art method, the samples must be processed with the following procedure.

(1) Samples collected in a fraction collector from a high performance liquid chromatograph are injected into sample containers.

(2) To remove the protonated solvent from each sample, it is evaporated, dried, and solidified.

(3) A given amount of deuterated solvent is dispensed.

(4) To mix the sample and the deuterated solvent well, the container is vibrated or the mixture is stirred.

(5) The sample dissolved in the deuterated solvent is transferred to a sample tube for NMR measurement.

(6) A label is stuck on the sample tube, and an NMR measurement is performed.

During the sequence of processing described above, when the step (1) is being executed, one must wait until all the samples are injected. Where one sample is taken in 15 minutes by fraction collection, one must wait for 24 hours if 96 samples are collected. If 192 samples are collected, one must wait for 48 hours. In this way, it takes a long time to pretreat samples. Furthermore, the steps (2)-(6) require cumbersome manual operations.

SUMMARY OF THE INVENTION

It is an object of the present invention to provide an analysis system which needs a sample pretreatment capable of being performed in a shortened time, automates cumbersome operations as much as possible, and permits efficient analysis.

This object is achieved in accordance with the teachings of the present invention by an analysis system comprising: a sample rack in which plural samples are accommodated; a sample container supply means for supplying sample containers; a sample aspirating-and-dispensing means for aspirating each sample from the sample tube in the sample rack and dispensing the sample into the sample container; a solvent-removing means for evaporating off a first solvent from sample containers and drying and solidifying the sample; a solvent dispensing means for dispensing a second solvent into each sample container; a sample-stirring means for stirring the mixture of the sample and the second solvent; a sample aspirating-and-transferring means for aspirating each sample dissolved in the second solvent and transferring the aspirated sample into a measuring portion; a sample recovery means for recovering the sample into the sample container from the measuring portion after measurement; a sample container recovery means for recovering the sample container in which the investigated sample has been recovered; and a control means for controlling the aforementioned various means.

In one feature of the present invention, the samples are successively and directly supplied from a high performance liquid chromatograph (HPLC) to the sample tubes of the sample rack in an analysis system.

In another feature of the present invention, the samples supplied from the high performance liquid chromatograph are taken into the sample tubes of the rack in a fraction collector and then supplied successively to the sample tubes in the sample rack in an analysis system.

In a further feature of the present invention, the aforementioned solvent-removing means comprises a sample container temperature-adjusting means for adjusting the temperature of the sample container to a desired temperature and a gas blowout means for blowing a regulated flow rate of gas against the sample, the gas being adjusted to a desired temperature.

In still another feature of the present invention, the above-described second solvent contains plural kinds, and the aforementioned solvent dispensing means is capable of selecting a desired one out of the plural kinds of the second solvent and dispensing the selected kind of the second solvent.

In yet another feature of the present invention, each sample aspirated and transferred by the sample aspirating-and-transferring means is subjected to measurement and then the sample is pushed out of the measuring portion by a gas under pressure, whereby the sample is recovered into the sample container.

In an additional feature of the present invention, the rack for holding the sample containers recovered by the sample container recovery means is of microplate size.

In a further additional feature of this analysis system, the samples are solutions containing the first solvent.

The present invention also provides an analysis method comprising the steps of: placing plural samples in a sample rack; supplying sample containers; aspirating each sample from the sample tube in the sample rack and dispensing the sample into the sample container; evaporating off a first solvent from each sample container and drying and solidifying the sample; dispensing a second solvent into each sample container; stirring each mixture of the sample and the second solvent; aspirating the sample and transferring the sample into a measuring portion; recovering the investigated sample into a sample container after measurement; and recovering the sample container in which the sample has been recovered.

In one feature of this analysis method, the system has a mode in which arbitrary ones of the steps can be skipped.

In another feature of this analysis method, the samples are solutions containing the first solvent.

Furthermore, the present invention provides an analysis system comprising: a sample container supply means for supplying sample containers each holding a sample therein; a solvent-removing means for evaporating off a first solvent-in the supplied sample containers and drying and solidifying each sample; a solvent dispensing means for dispensing a second solvent into each sample dried and solidified; a sample-stirring means for stirring each sample containing the second solvent; a sample aspirating-and-transferring means for aspirating each sample dissolved in the second solvent and transferring the aspirated sample into a measuring portion; a sample recovery means for recovering the sample into a sample container from the measuring portion after measurement; a sample container recovery means for recovering the sample container in which the investigated sample has been recovered; and a control means for controlling the above-described various means.

In one feature of this analysis system, the aforementioned solvent-removing means comprises a sample temperature-adjusting means for adjusting the sample container to a desired temperature and a gas blowout means for blowing a regulated flow rate of gas against the sample, the gas being adjusted to a desired temperature.

In another feature of this analysis system, the above-described solvent dispensing means can select a desired one out of plural kinds of the second solvent and dispense it.

In a further feature of this analysis system, the sample aspirated and transferred by the aspirating-and-transferring means is subjected to measurement, and then the sample is pushed out of the measuring portion by a gas under pressure, whereby the sample is recovered into a sample container.

In an additional feature of this analysis system, the rack for accommodating the sample containers recovered by the sample container recovery means is of microplate size.

In a further additional feature of this analysis system, the samples are solutions containing the first solvent.

In addition, the present invention provides an analysis method comprising the steps of: supplying sample containers each holding a sample therein; evaporating off a first solvent from the sample in each supplied sample container and drying and solidifying the sample; dispensing a second solvent into each sample dried and solidified; stirring each sample in which the second solvent has been dispensed; aspirating each sample dissolved in the second solvent and transferring the sample into a measuring portion; recovering each sample into a sample container from the measuring portion after measurement; and recovering the sample container in which the investigated sample has been recovered.

In one feature of this analysis method, the system has a mode in which any arbitrary one of the steps can be skipped.

In another feature of this analysis method, the samples are solutions containing the first solvent.

Further, the present invention provides an analysis system comprising: a sample container supply means for supplying sample containers each holding a sample therein; a solvent dispensing means for dispensing a second solvent into each sample container; a sample-stirring means for stirring each sample in which the second solvent has been dispensed; a sample aspirating-and-transferring means for aspirating each sample dissolved in the second solvent and transferring the sample into a measuring portion; a sample recovery means for recovering the sample into a sample container from the measuring portion after measurement; a sample container recovery means for recovering each sample container in which the investigated sample has been recovered; and a control means for controlling the above-described various means.

In one feature of this analysis system, the above-described solvent dispensing means can select a desired one out of plural kinds of the second solvent and dispense it.

In a further feature of this analysis system, the sample aspirated and transferred by the aspirating-and-transferring means is subjected to measurement and then pushed out of the measuring portion by a gas under pressure, whereby the sample is recovered into sample container.

In an additional feature of this analysis system, the rack for holding the sample containers recovered by the sample container recovery means is of microplate size.

In a further additional feature of this analysis system, the samples are solutions dissolved in the second solvent or are a solid.

Moreover, the present invention provides an analysis method comprising the steps of: supplying sample containers each containing a sample therein; dispensing a second solvent into the sample container; stirring the sample in which the second solvent has been dispensed; aspirating each sample containing the second solvent and transferring the sample into a measuring portion; recovering each sample into a sample container from the measuring portion after measurement; and recovering the sample containers in which investigated sample has been recovered.

In one feature of this analysis method, the system has a mode in which arbitrary ones of the steps can be skipped.

In another feature of this analysis method, the samples are solutions dissolved in the second solvent or are a solid.

In a further feature of this analysis system, the first and second solvents are a protonated solvent and a deuterated solvent, respectively.

In a further feature of this analysis method, the first and second solvents are a protonated solvent and a deuterated solvent, respectively.

In still another feature of this analysis system, the various means described above are set at the site of given positions on a turntable, and the sequence of the sample treatments is made to progress by incrementally rotating the turntable carrying the sample containers thereon.

In still another feature of this analysis method, the various steps described above are carried out in given positions on a turntable, and the sequence of the steps is made to progress by incrementally rotating the turntable carrying the sample containers thereon.

Other objects and features of the present invention will appear in the course of the description thereof, which follows.

DESCRIPTION OF THE PREFERRED EMBODIMENTS

Figure 1:
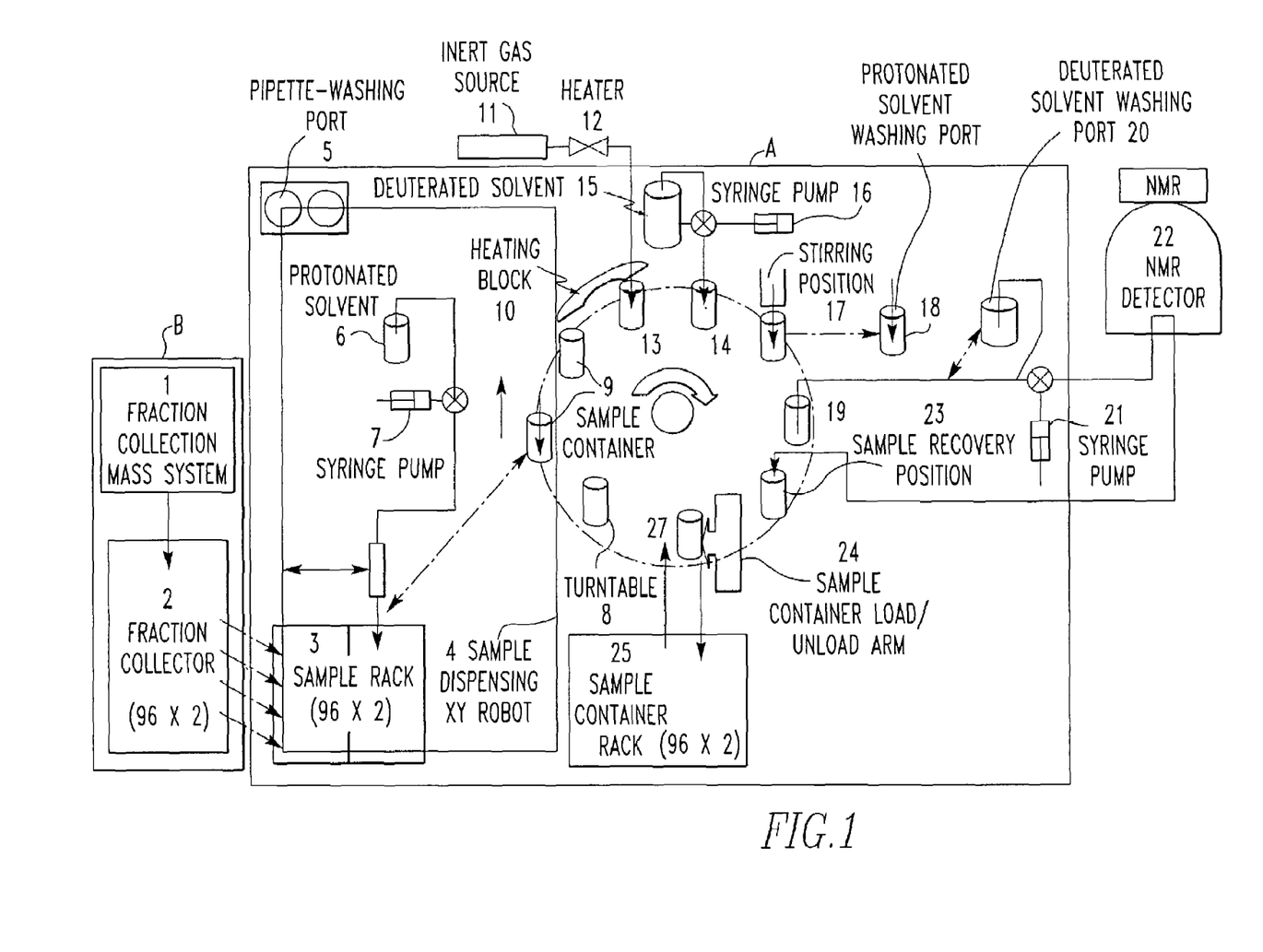
FIG. 1 is a block diagram of an analysis system in accordance with the present invention.

Embodiments of the present invention are hereinafter described with reference to the accompanying drawings. FIG. 1 is a block diagram of an analysis system in accordance with the present invention. The analysis system, indicated by A, is supplied with samples from an external system B, automatically pretreats the samples, and performs their analysis.

The samples separated as the fractions by a high performance liquid chromatograph (HPLC) are taken into the test tubes in a rack in a fraction collector 2 by a fraction collection mass system 1. Information for identification is automatically given to each sample separated. Where individual samples are taken by fraction collection, when the sample is injected into the sampler of the high performance liquid chromatograph, a start signal is generated. When the separation step of the liquid chromatograph ends, an end signal is generated. When the individual sample separated as a fraction is taken into the fraction collector 2, a fraction collection signal is generated. The fraction collector 2 has sample racks for accommodating samples taken by the fraction collection mass system 1. Microplates or racks for receiving 96×2 samples are used in the fraction collector 2.

Two sample racks 3 are included within the present analysis system. The fraction collection mass system 1 and the fraction collector 2 together form the system B external to the present analysis system A. Since systems A and B are computer controlled normally at different speeds, the systems A and B are not synchronous with each other. Therefore, it is necessary to transfer samples at one time from the fraction collector 2 into the sample rack 3 within the present analysis system A. For this purpose, the sample racks 3 are used. The sample racks 3 can receive 96×2 samples. To minimize the size, sample tubes each having an outside diameter of 12 mm and a length of about 120 mm are used.

In transferring samples from the fraction collector 2 external to the present analysis system A to the sample rack 3, the fraction collector 2 is placed at a higher position than the sample rack 3. The bottom of the test tubes of the rack in the fraction collector 2 are connected to the top of the sample tubes in the sample rack 3 by Teflon tubes. Flow is induced automatically and in real time by making use of the height difference and pressure application. Of course, the rack of the fraction collector 2 holding samples therein may be manually transferred to the sample rack 3, i.e., off-line.

A sample dispensing XY robot 4 aspirates a given amount of sample from the sample tube of the sample rack 3, dispenses the sample into sample container 9 on a turntable 8. The amount of each sample can be pre-set at will. Whenever dispensing of each sample is completed, the outside of the pipette of the sample dispensing XY robot 4 is washed with a protonated solvent, such as methanol or acetone at a pipette-washing port 5. The inside of the pipette is washed with a protonated solvent 6. A syringe pump 7 is used to aspirate and dispense the samples. The pump 7 can be set to a desired amount, for example, such as 0.5 ml, 1 ml, or 2 ml.

The turntable 8 is provided with holes in which sample containers are inserted. The turntable 8 is made up of three disks that are vertically, regularly spaced from each other in order to insert the sample container into the sample hole easily and smoothly. The three disks rotate as a unit incrementally. The sample dispensing XY robot 4 dispenses the sample into twelve sample containers at the sample dispensing position 9 on the turntable 8. Necessary processing is subsequently performed in various positions. The instrument has a mode in which the sample is processed by skipping intermediate unnecessary process steps. The number of sample containers on the turntable 8 may be increased from 12 to 24 or more.

Figure 2:
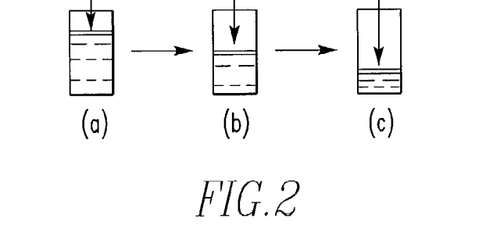
FIG. 2 is a diagram illustrating the length of a nozzle for blowing out heated nitrogen gas.

A heating block 10 heats the sample containers on the turntable 8 with a temperature ranging from room temperature to about 80° C. to promote evaporation of the protonated solvent. The heating block 10 can be set at any desired temperature. The instrument further includes an inert gas source 11 for supplying an inert gas, such as nitrogen gas or argon gas. A heater 12 is attached to the turntable 8. In a heating and evaporation position 13, the inert gas heated from room temperature to about 80° C. is blown against the liquid surface of each sample to accelerate evaporation of the protonated solvent. At this time, the heating temperature can be set at will. Also, the amount of inert gas blown on the liquid surface can be varied at will. This process step can be repeated three times or so. As illustrated in FIG. 2, as the process sequence progresses, successively longer nozzles are used to blow the gas as indicated by (a), (b), and (c) of FIG. 2 such that the whole sample within each sample container 9 is heated uniformly. The three nozzles have been integrated such that they can be simultaneously lowered and inserted into three sample containers.

After the protonated solvent is evaporated off and each sample is dried and solidified, a syringe pump 16 dispenses a given amount of a deuterated solvent, such as deuterated acetone or deuterated methanol, into each container in a deuterated solvent dispensing position 14. At this time, the amount of dispensed deuterated solvent can be set to 0.5 ml, 0.25 ml, 0.12 ml, 0.06 ml, or any other arbitrary amount. Then, each sample and the deuterated solvent are mixed well in a stirring position 17 with a stirring means, such as a stirring propeller, an ultrasonic stirrer, or vibrating vortex mixer. After the stirring, the stirring propeller is washed in a protonated solvent washing port 18. The stirring propeller is sufficiently rotated idly in air after the washing to sufficiently dry the propeller. Then, a given amount of sample is aspirated from the sample container 9 in a sample injection position 19 (i.e., aspirating and transferring position) by another syringe pump 21 via a pipette, and the sample is injected into an NMR detector 22.

A flow NMR detector having a sample passage therein is used as this NMR detector 22. At this time, the amount of injected sample can be set to 0.5 ml, 0.25 ml, 0.12 ml, 0.06 ml, or any other arbitrary amount. To inject the sample into the NMR detector 22 wastelessly, an amount of deuterated solvent corresponding to the dead volume of the connector tube is injected after the sample injection. In this way, the sample is completely fed into the NMR detector 22 from the connector tube. After the end of the injection, a start trigger signal is sent to an NMR spectrometer to start an NMR measurement. During the measurement, the outside and inside of the injecting pipette are washed at a deuterated solvent washing port 20.

Plural kinds of detectors having different internal volumes can be used as the NMR detector 22. For example, these detectors have internal volumes of 0.5 ml, 0.25 ml, 0.12 ml, and 0.06 ml, respectively. The injecting pipette can arbitrarily vary the amount of injected deuterated solvent according to the internal volume of the detector. The end of the sample passage of the NMR detector 22 is placed in a sample recovery position 23. After the end of the measurement, the investigated sample is recovered into a sample container. At this time, the sample is sent by injecting a deuterated solvent to supply the sample and to wash the NMR detector 22 and sample passages before and behind the detector. At this time, the amount of the injected deuterated solvent can be set to 1.0 ml, 0.5 ml, 0.25 ml, or any other arbitrary amount.

Each sample container holding the recovered sample therein is recovered to a sample container rack 25 by a sample container load/unload arm 24. New empty sample containers are supplied onto the unloaded turntable 8 from the sample container rack 25. At this time, 96×2–192 sample containers are placed on the sample container rack 25. Thus, both empty, unused sample containers and sample containers holding recovered and investigated samples therein exist.

An optical sensor (not shown) is mounted under a sample container supply position 27 on the turntable 8. If no new sample container is supplied to this position from the sample container load/unload arm 24, the optical sensor detects it, and the subsequent steps including sample aspirating-and-dispensing, heating, evaporation with heated inert gas, dispensing a deuterated solvent, stirring, injection of sample into the NMR detector, and recovery of sample from the NMR detector are all withheld.

Figure 3:
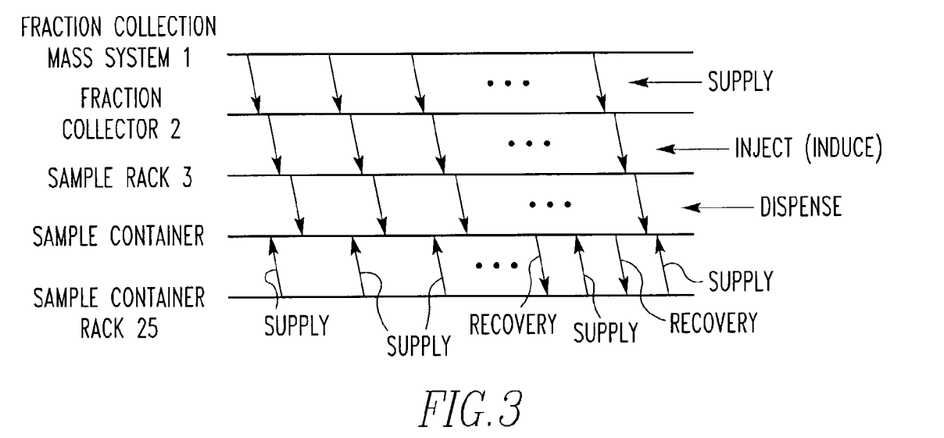
FIG. 3 is a diagram illustrating a sequence of operations for injecting and recovering samples.

The operation of the present analysis system is next described. FIG. 3 is a diagram illustrating a sequence of operations for injecting and recovering samples. Samples are successively supplied from the fraction collection mass system 1 to the fraction collector 2. Concurrently, the samples are injected (i.e., induced) into the sample tubes in the sample rack 3 from the bottom of the test tubes of the rack in the fraction collector 2 through the Teflon tubes in communication with the sample tubes in the sample racks 3. New, empty sample containers are successively placed onto the turntable 8 from the sample container rack 25. The sample dispensing XY robot 4 dispenses the sample into the sample container 9. The resulting sample is dried, stirred, and otherwise processed on the turntable 8. After the sample is supplied to the NMR spectrometer, the sample container 9 in which the investigated sample has been recovered is sent back to the sample container rack 25 from the turntable 8.

Figure 4:
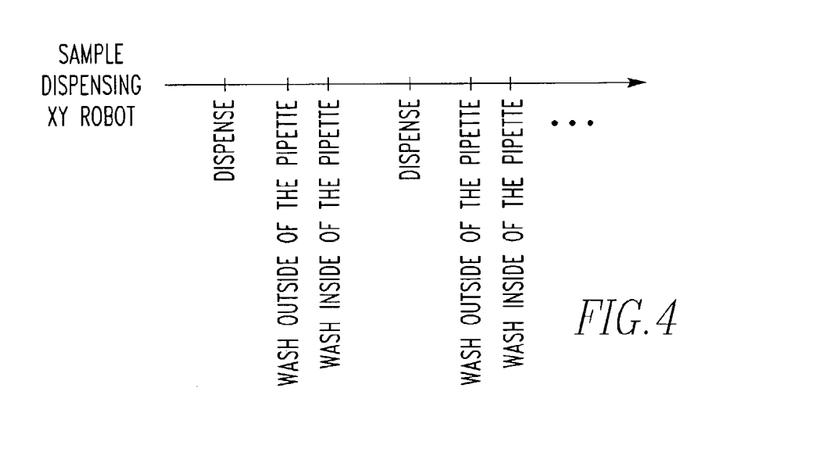
FIG. 4 is a diagram illustrating the operation of a sample dispensing XY robot.

FIG. 4 is a diagram illustrating the operation of the sample dispensing XY robot 4. This robot 4 aspirates a given amount of sample from the sample rack 3 and dispenses the sample into a sample container 9 on the turntable 8. Then, the outside and inside of the pipette are washed. Subsequently, the next sample is dispensed into a new sample container. Thereafter, these operations are repeated. In the example of FIG. 4, the outside of the pipette of the dispensing XY robot 4 is first washed, followed by washing of the inside. The order may be reversed. After the washing, a dry inert gas, such as nitrogen gas or argon gas, may be blown against the outside of the pipette to promote drying of the pipette.

Figure 5:
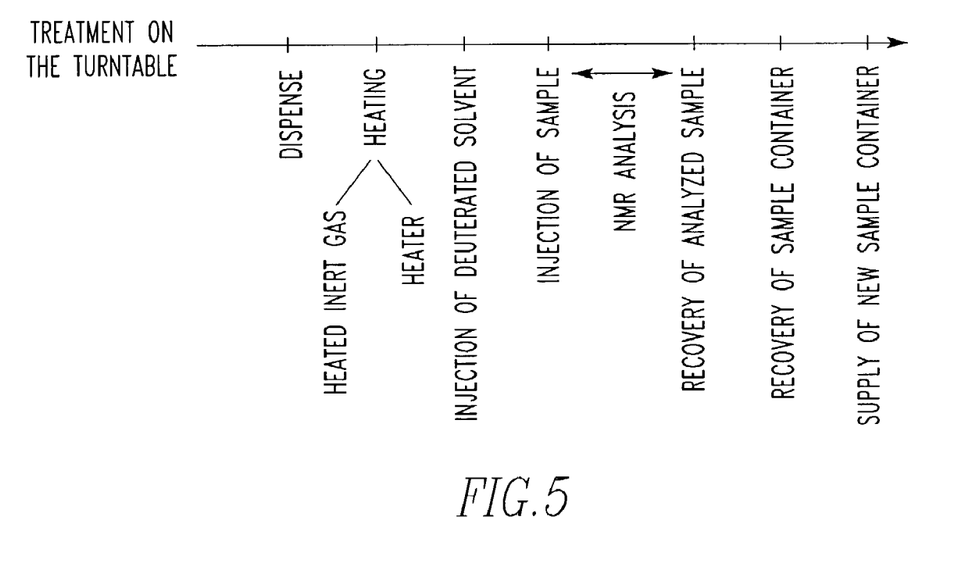
FIG. 5 is a diagram illustrating the time sequence of processing for one sample container on a turntable.

FIG. 5 is a diagram illustrating the time sequence at which each sample container on the turntable is processed. The sample container 9 holding a sample therein is heated by the heating block 10. At the same time, a heated inert gas is blown against the container. The protonated solvent is evaporated off and the sample is dried and solidified. Then, a deuterated solvent is dispensed into the dried solid sample. The mixture is stirred and dissolved. Thereafter, the sample is injected into the NMR detector 22. After NMR measurement in the NMR detector 22, the investigated sample is recovered into a sample container. The sample container holding the recovered sample is recovered into the sample container rack 25. At the same time, a new, empty sample container is supplied onto the turntable 8 from the sample container rack 25.

The above-described process steps are controlled by a control unit, such as a computer (not shown). The control sequence can be modified variously according to a control program. For example, in the above embodiment, the turntable 8 is rotated in increments, and the process steps are carried out successively. A mode in which some intermediate process steps are skipped may be provided, and process steps can be selectively carried out, if necessary.

In the above description, supply of samples from the fraction collector 2 to the sample rack 3 is automatically done in real time on-line. After all samples are stored in the fraction collector 2, all the samples may be manually transferred to the sample rack 3, and then processing as described above may be carried out. That is, off-line processing may be performed.

Furthermore, in the above description, the sample dispensing XY robot 4 conveys a sample from the sample rack 3 and dispenses the sample into sample container 9 on the turntable 8. In this way, process steps are carried out in succession. If the samples have been previously dissolved in a deuterated solvent, each sample container 9 holding a sample therein may be set on the sample container rack 25. The sample container 9 may be placed on the turntable 8 by the sample container load/unload arm 24, and the process may jump to the step for injecting the sample into the NMR detector 22 by skipping all the intermediate process steps. That is, each sample container holding a sample is placed onto the turntable 8 from the sample container rack 25 by the sample container load/unload arm 24, the sample container is conveyed directly into the sample injection position 19 while skipping all the intermediate process steps including heating, drying, dispensing of a deuterated solvent, and stirring. The sample is injected into the NMR detector 22. After NMR measurement, the investigated sample is recovered in the sample recovery position 23. The sample container holding the recovered sample is recovered to the sample container rack 25. The sample container 9 holding the next sample is placed onto the turntable 8 from the sample container rack 25, and then the above-described processing is repeated.

If the sample contained in each sample container 9 is in powdered form or a bulk solid, each sample container 9 holding a sample is previously set on the sample container rack 25, and then the sample container 9 is gripped by the sample container load/unload arm 24. The sample container 9 is placed on the turntable 8, and then the process directly goes to the step for dispensing a deuterated solvent and stirring and dissolving the mixture by skipping all of the sample dispensing steps using the sample dispensing XY robot 4, the heating step using the heating block 10, and the solvent removing step using blowing with heated inert gas. Then, the sample container 9 is transferred into the sample injection position 19, and the sample is injected into the NMR detector 22. After NMR measurement, the investigated sample is recovered in the sample recovery position 23. The sample container 9 holding the recovered sample therein is then recovered to the sample container rack 25. Thereafter, the sample container 9 is placed onto the turntable 8 from the sample container rack 25. Then, the above-described process steps may be repeated in succession.

An example in which selected process steps are skipped according to various purposes has been described thus far. Obviously, the present invention can also be applied to a simpler analysis system from which the various means for performing these skipped process steps have been omitted and thus the analysis system has been specialized for a certain purpose. One example of this simpler analysis system is an instrument which is used only off-line and in which the interface to a high performance liquid chromatograph is omitted and the sample rack holding samples is manually supplied. Another example is a dedicated instrument which is used for only solid samples and from which the interface to a high performance liquid chromatograph and the protonated solvent-removing means have been omitted.

In the above embodiment, an investigated sample is recovered into the sample container into which a sample was first dispensed. The present invention is not limited to this method. For example, new sample containers may be prepared, and analyzed samples may be recovered into these unused sample containers.

Figure 6:
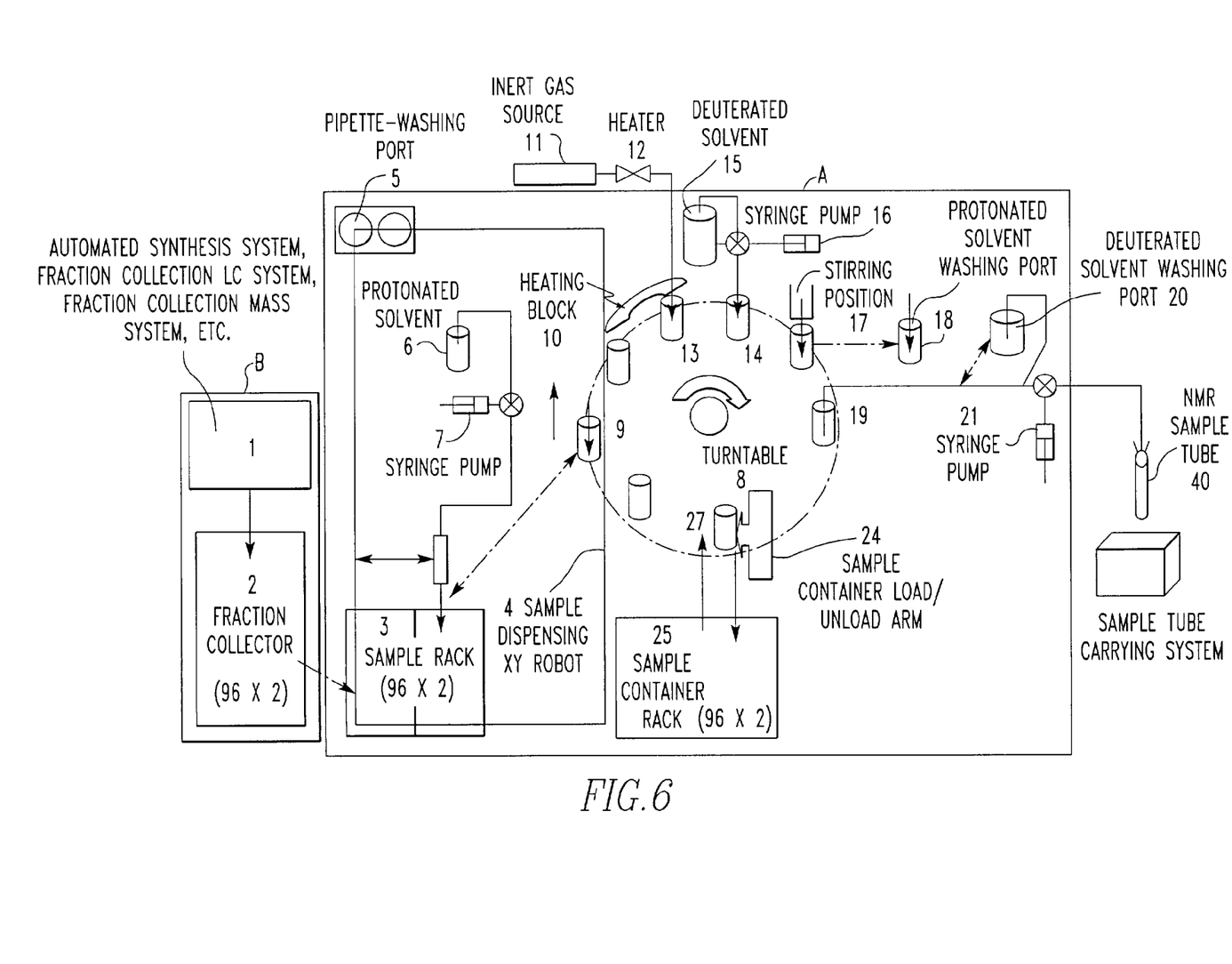
FIG. 6 is a block diagram of another system in accordance with the present invention.

FIG. 6 is a block diagram of another analysis system in accordance with the present invention. This system is similar to the analysis system already described in connection with FIG. 1 except that a sample is not injected into the NMR detector 22 but into an NMR sample tube 40 and that the injected sample is not recovered into a sample container. With this system, measurements are performed in other locations. Therefore, the present analysis system merely acts as an automatic injecting system for automatically injecting samples into sample tubes. The present analysis system may also have a mode in which only necessary processing steps are performed without performing intermediate unnecessary steps. The analysis system may also be an off-line instrument that does not perform on-line processing (i.e., samples are automatically supplied from the fraction collector 2 to the sample rack 3 in real time) but performs off-line processing (i.e., after all samples are supplied to the fraction collector 2, all samples are manually transferred to the sample rack 3 and then the aforementioned processing is carried out).

Figure 7:
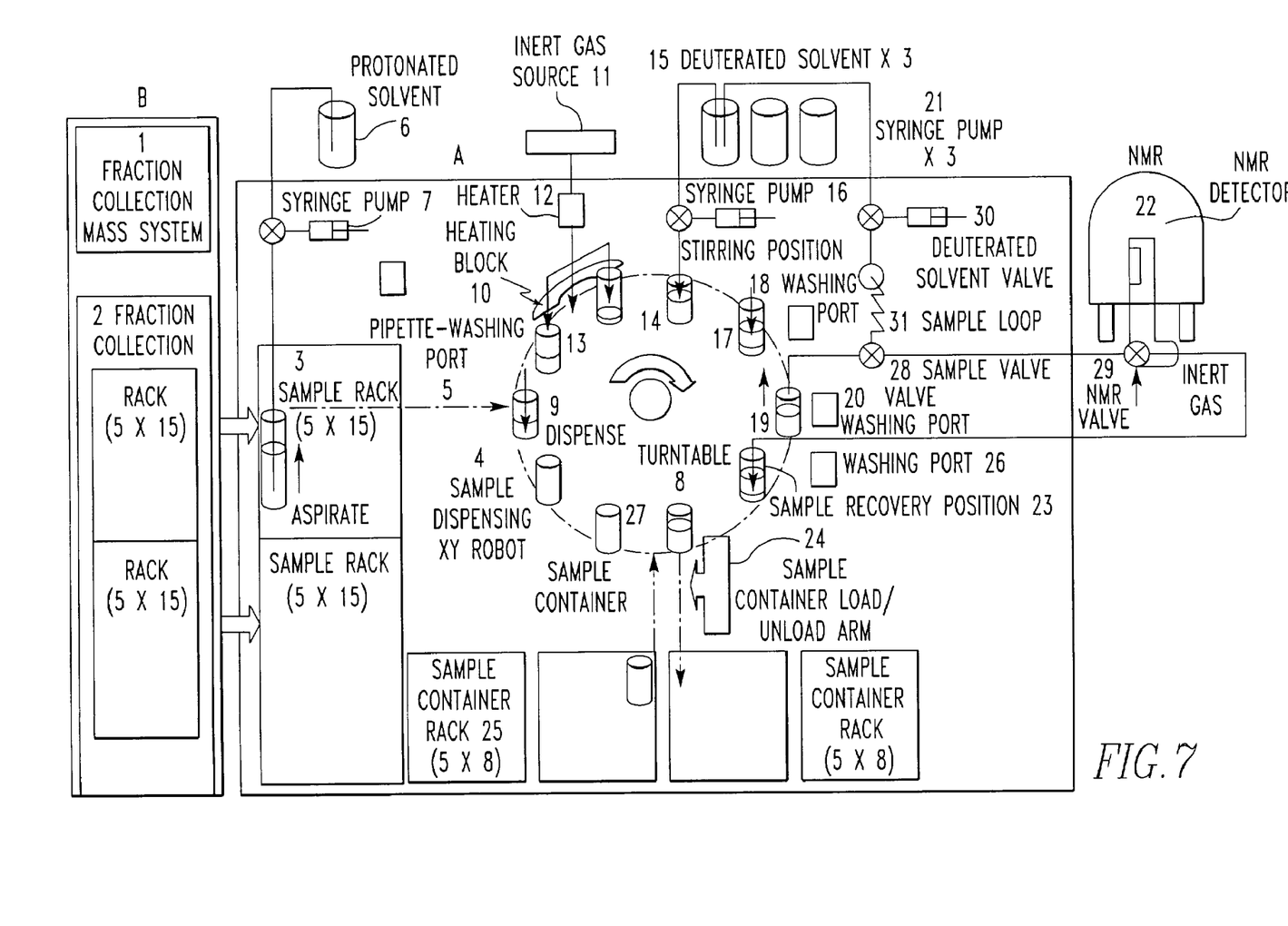
FIG. 7 is a block diagram of a further system in accordance with the present invention.

FIG. 7 is a block diagram of a further analysis system in accordance with the present invention. This analysis system is similar to the analysis system previously described in connection with FIG. 1 except for the following points (1)-(7).

(1) The fraction collector 2 and the sample racks 3 can be of such sizes that they can receive 75×2 samples.

(2) A deuterated solvent selector valve (not shown in FIG. 7) is provided to select any desired one that can be dispensed into a sample container 9 out of plural kinds (three kinds in the example of FIG. 7) of deuterated solvent.

(3) A sample valve 28 is provided to inject a sample into the NMR detector 22. First, a sample is drawn in from a sample container 9 and held in a sample loop 31. Then, a deuterated solvent is drawn in from the deuterated solvent reservoir 15 and held in the syringe pump 21. Thereafter, the aspirated deuterated solvent is forced toward the sample loop 31 to thereby force the sample held in the sample loop 31 toward the NMR detector 22.

(4) When a sample is injected into the NMR detector 22, any desired injection solvent can be selected by changing a deuterated solvent selector valve 30.

(5) An NMR valve 29 is mounted between the sample valve 28 and the NMR detector 22. When an investigated sample is recovered from the NMR detector 22, a cheap inert gas, such as nitrogen gas or argon gas, is directly blown in from the NMR valve 29 to push the sample forward instead of injecting an expensive deuterated solvent for the same purpose. This saves the amount of expensive deuterated solvent consumed.

(6) After an investigated sample is recovered into a sample container 9 by blowing in an inert gas, the inside of the sample passage inside the NMR detector 22 is washed using the deuterated solvent left between the sample valve 28 and the NMR valve 29. After the washing, the deuterated solvent is vented into a washing port 26.

(7) To permit the sample inside each sample container 9 to be evaporated, dried, and solidified by a commercially available centrifugal evaporator, each recovered sample container 9 can be installed on the centrifugal evaporator together with the sample container rack 25. For this purpose, four racks capable of holding 40×4 samples are used to match the size of the sample container rack 25 to the microplate size.

The present analysis system can also have a mode in which some intermediate process steps are skipped. Only necessary process steps may be selectively done. Furthermore, this analysis system may be designed not as an on-line analysis system in which samples are supplied automatically from the fraction collector 2 to the sample rack 3 in real time, but as an off-line analysis system in which all samples are manually transferred to the sample rack 3 and the subsequent processing as described above is carried out after supplying all the samples to the fraction collector 2.

Figure 8:
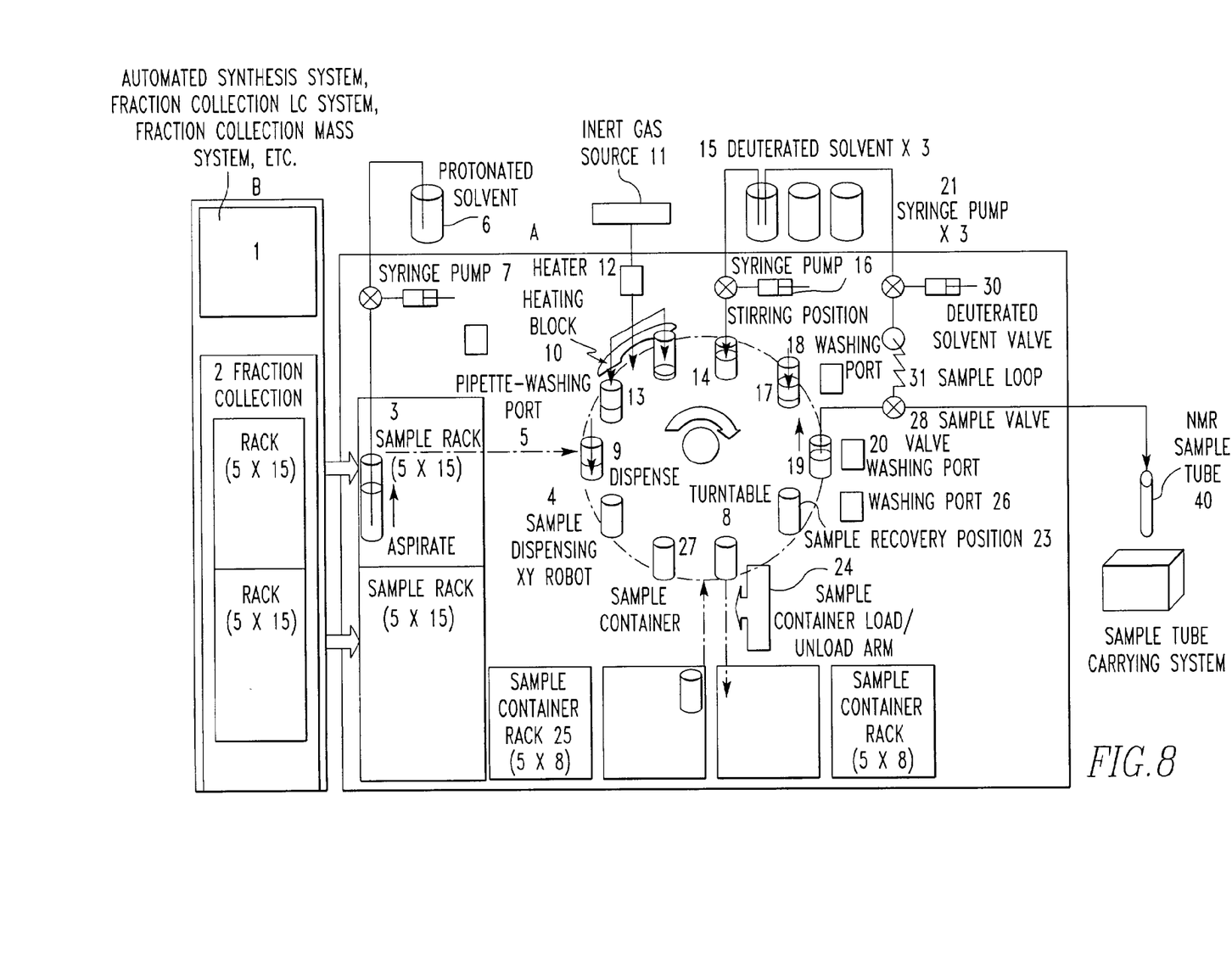
FIG. 8 is a block diagram of a yet another system in accordance with the present invention.

FIG. 8 is a block diagram of a further system in accordance with the present invention. This system is similar to the system already described in connection with FIG. 7 except that a sample is injected not into the NMR detector 22 but into the NMR sample tube 40 and that the injected sample is not recovered into a sample container. With this system, measurements are effected in another location. Therefore, the present analysis system merely functions as an automatic injecting system for injecting samples into sample tubes automatically. The present analysis system may also have a mode in which some intermediate process steps can be skipped; only required process steps are selectively performed. In addition, the present analysis system may be designed not as an on-line instrument in which samples are automatically supplied from the fraction collector 2 to the sample rack 3 in real time, but as an off-line instrument in which all samples are supplied into the fraction collector 2, then all samples are manually transferred to the sample rack 3, and the subsequent processing as described above is performed.

In this way, the present analysis system carries out the steps:

(1) Samples stored successively in the fraction collector are dispensed into sample containers in real time. Consequently, the sequence can quickly proceed to the next step.

(2) After the required amount of sample is dispensed into the sample container, the protonated solvent is evaporated off by heating using a heating block and by blowing a heated inert gas against the containers. Thus, the samples are dried and solidified.

(3) A given amount of deuterated solvent corresponding to the internal volume of the NMR detector is dispensed into each dried sample.

(4) The mixture is stirred so that the sample dissolves well in the deuterated solvent.

(5) An amount of sample necessary for NMR measurement is injected into the NMR detector.

(6) After a sample is injected into the NMR detector, a measurement is started by giving a start trigger to the NMR instrument.

Since the steps (1)-(6) are carried out fully automatically, the throughput is improved greatly. The user is relieved of cumbersome operations.

In cases other than the case in which samples are supplied on-line from the fraction collector 2 to the sample rack 3, if all the samples are supplied to the sample rack 3 off-line, the throughput is improved by similarly automating the processing later than the supply. Hence, the user is relieved of cumbersome operations. Furthermore, in cases other than the case in which a sample is injected into the NMR detector 22, automatically injecting a sample into the NMR sample tube 40 assists in performing NMR measurement in another location. This relieves the user of cumbersome operations.

In the present invention, a replacing solvent is not limited to a deuterated solvent. Obviously, if a desired protonated solvent is prepared, the instrument is useful as an automating instrument for replacing the sample in various apparatus (e.g., mass spectrometer, spectroscopic instrument, and various analysis instruments) by a protonated solvent, as well as for replacing the sample by a deuterated solvent during NMR measurement.

As described thus far, the present invention shortens the pretreatment prior to analysis and relieves the user of cumbersome operations to thereby improve the efficiency of the work.

Having thus described our invention with the detail and particularity required by the Patent Laws, what is desired protected by Letters Patent is set forth in the following claims.

What is claimed is:

1. An analysis system comprising:
    a sample rack in which plural samples dissolved in protonated solvent are accommodated;
    a turntable for carrying sample containers and incrementally rotating to present the sample containers at various stations;
    a sample container supply means for supplying sample containers;
    a sample aspirating-and-dispensing means for aspirating each sample from said sample rack and dispensing said sample into said sample container;
    a solvent-removing means for evaporating off the protonated solvent from each sample and drying and solidifying the sample comprising nozzles for removal of the solvent by injecting gas into the sample container, the depth of the insertion of the nozzles into the sample container being increased as the progress of removal;
    a source of deuterated solvent;
    a solvent-dispensing means for dispensing a deuterated solvent from said source into each dried and solidified sample;
    a sample-stirring means for stirring the sample in which said deuterated solvent has been dispensed;
    a sample aspirating-and-transferring means for aspirating each sample dissolved in said deuterated solvent and transferring sample into a measuring portion;
    a sample recovery means for recovering the sample into a sample container from said measuring portion after measurement;
    a sample container recovery means for recovering the sample container in which the investigated sample has been recovered; and
    a control means for sequentially controlling the operation of the analysis system throughout sample processing.

2. The analysis system of claim 1, wherein said plural samples are successively supplied from a high performance liquid chromatograph.

3. The analysis system of claim 2, wherein the samples supplied from said high performance liquid chromatograph are separately taken into a fraction collector of said high performance liquid chromatograph and then supplied successively to a sample rack via tubes in communication with said sample rack.

4. The analysis system of claim 1, wherein said solvent-removing means comprises a sample container temperature-adjusting means for adjusting the temperature of the sample container to a desired temperature and a gas blowout means for blowing a regulated flow rate of gas against the sample, the gas being adjusted to a desired temperature.

5. The analysis system of claim 1, wherein said deuterated solvent contains plural kinds, and wherein said solvent-dispensing means is capable of selecting a desired one out of the plural kinds of said deuterated solvent and dispensing the selected kind of said second solvent.

6. The analysis system of claim 1, wherein each sample aspirated and transferred by said sample aspirating-and-transferring means is subjected to measurement and then the sample is pushed out of the measuring portion by a gas under pressure, whereby the sample is recovered into a sample container.

7. The analysis system of claim 1, wherein the rack for holding the sample container recovered by said sample container recovery means is of microplate size.

8. The analysis system of claim 1, wherein said samples are solutions including said first solvent.

9. An analysis system comprising:
    a sample container supply means for supplying sample containers each holding a sample dissolved in protonated solvent therein;
    a turntable for carrying sample containers and incrementally rotating to present the sample containers at various stations;
    a solvent-removing means for evaporating off the protonated solvent in the supplied sample containers and drying and solidifying each sample comprising nozzles for removal of the solvent by injecting gas into the sample container, the depth of the insertion of the nozzles into the sample container being increased as the progress of removal;
    a source of deuterated solvent;
    a solvent-dispensing means for dispensing a deuterated solvent from said source into each dried and solidified sample;
    a sample-stirring means for stirring each sample in which said deuterated solvent has been dispensed;
    a sample aspirating-and-transferring means for aspirating each sample dissolved in said deuterated solvent and transferring the aspirated sample into a measuring portion;
    a sample recovery means for recovering the sample into a sample container from said measuring portion after measurement;
    a sample container recovery means for recovering the sample containers in which the investigated samples have been recovered; and
    a control means for sequentially controlling the above-described operation of the analysis system throughout sample peocessing.

10. The analysis system of claim 9, wherein said solvent-removing means comprises a sample container temperature-adjusting means for adjusting the temperature of the sample container to a desired temperature and a gas blowout means for blowing a regulated flow rate of gas against the sample, the gas being adjusted to a desired temperature.

11. The analysis system of claim 9, wherein said deuterated solvent contains plural kinds, and wherein said solvent-dispensing means is capable of selecting a desired one out of the plural kinds of said deuterated solvent and dispensing it.

12. The analysis system of claim 9, wherein the sample aspirated and transferred by said aspirating-and-transferring means is subjected to measurement and then the sample is pushed out of the measuring portion by a gas under pressure, whereby the sample is recovered into the sample container.

13. The analysis system of claim 9, wherein a rack for accommodating the sample containers recovered by said sample container recovery means is of microplate size.

14. The analysis system of claim 9, wherein said samples are solutions including said first solvent.

15. An analysis system comprising:
  a sample container supply means for supplying sample containers each holding a sample dissolved in protonated solvent therein;
  a turntable for carrying sample containers and incrementally rotating to present the sample containers at various stations;
  a solvent-removing means for evaporating off a first solvent from each sample and drying and solidifying the sample comprising nozzles for removal of the solvent by injecting gas into the sample container, the depth of the insertion of the nozzles into the sample container being increased as the progress of removal;
  a source of deuterated solvent;
  a solvent-dispensing means for dispensing a deuterated solvent from said source into each sample container;
  a sample-stirring means for stirring each sample in which said deuterated solvent has been dispensed;
  a sample aspirating-and-transferring means for aspirating each sample dissolved in said deuterated solvent and transferring the sample into a measuring portion;
  a sample recovery means for recovering the sample into a sample container from said measuring portion after measurement;
  a sample container recovery means for recovering each sample container in which the investigated sample has been recovered; and
  a control means for sequentially controlling the above-described operation of the aanlysis system throughpout sample processing.

16. The analysis system of claim 15, wherein said deuterated solvent contains plural kinds, and wherein said solvent-dispensing means is capable of selecting a desired one out of the plural kinds of said deuterated solvent and dispensing it.

17. The analysis system of claim 15, wherein the sample aspirated and transferred by said aspirating-and-transferring means is subjected to measurement and then pushed out of said measuring portion by a gas under pressure, whereby the sample is recovered into said sample container.

18. The analysis system of claim 15, wherein the rack for holding the sample containers recovered by said sample container recovery means is of microplate size.

19. The analysis system of claim 15, wherein the samples are solutions dissolved in said deuterated solvent or are a solid.

* * * * *

UNITED STATES PATENT AND TRADEMARK OFFICE
CERTIFICATE OF CORRECTION

PATENT NO. : 7,270,783 B2 Page 1 of 1
APPLICATION NO. : 10/004259
DATED : September 18, 2007
INVENTOR(S) : Takase et al.

It is certified that error appears in the above-identified patent and that said Letters Patent is hereby corrected as shown below:

Column 12, lines 57-58, Claim 9, delete [[above-described]]

Column 12, line 59, Claim 9, "peocessing" should read -- processing --

Column 14, line 11, Claim 15, "aanalysis system throughpout" should read -- analysis system throughout --

Signed and Sealed this

Fifteenth Day of April, 2008

JON W. DUDAS
*Director of the United States Patent and Trademark Office*